(12) United States Patent
Smith

(10) Patent No.: US 6,719,699 B2
(45) Date of Patent: Apr. 13, 2004

(54) ADHESIVE HYDROPHILIC MEMBRANES AS COUPLANTS IN ULTRASOUND IMAGING APPLICATIONS

(75) Inventor: Larry L. Smith, Seattle, WA (US)

(73) Assignee: Sonotech, Inc., Bellingham, WA (US)

(*) Notice: Subject to any disclaimer, the term of this patent is extended or adjusted under 35 U.S.C. 154(b) by 0 days.

(21) Appl. No.: 10/071,777

(22) Filed: Feb. 7, 2002

(65) Prior Publication Data

US 2003/0149359 A1 Aug. 7, 2003

(51) Int. Cl.[7] .................................................. A61B 8/14
(52) U.S. Cl. ...................................................... 600/459
(58) Field of Search ................................ 600/407, 437, 600/439, 438, 440, 441–459, 461–471; 73/625, 618, 626, 644; 128/916; 607/152; 601/2; 604/20

(56) References Cited

U.S. PATENT DOCUMENTS

| | | |
|---|---|---|
| 4,699,146 A | 10/1987 | Sieverding |
| 5,394,877 A | 3/1995 | Orr et al. |
| 5,522,878 A | 6/1996 | Montecalvo et al. |
| 5,782,767 A | 7/1998 | Pretlow, III |
| 6,005,039 A | 12/1999 | Sulc et al. |
| 6,039,694 A | 3/2000 | Larson et al. |
| 6,217,894 B1 | 4/2001 | Sawhney et al. |
| 6,478,739 B1 * | 11/2002 | Hong .......................... 600/437 |

* cited by examiner

*Primary Examiner*—Ali M. Imam
(74) *Attorney, Agent, or Firm*—Robert L. McDowell

(57) ABSTRACT

Adhesive hydrogel films as ultrasound couplants wherein such hydrogels are adhesive on both sides for adhering to an ultrasound probe and to a protective sleeve or probe cover which facilitates acoustic coupling between an object such as between the human body and the active area of an ultrasound probe, thereby eliminating the requirement for coupling gels and fluids within the sleeve or cover.

4 Claims, 1 Drawing Sheet

ADHESIVE HYDROPHILIC MEMBRANES AS COUPLANTS IN ULTRASOUND IMAGING APPLICATIONS

FIELD OF THE INVENTION

The present invention is directed to the medical use of ultrasound acoustic energy for imaging, doppler based flow measurement, and therapy. In particular, the present invention pertains to the use of adhesive, acoustic self-coupling hydrogels to couple sound between ultrasound transducers and protective sheaths or covers.

BACKGROUND OF THE INVENTION

Ultrasound, as used for medical applications, utilizes high frequencies, typically between 1 and 30 MHz for imaging and flow measurements and between 0.050 and 1.00 MHz for therapy, all of which are poorly transmitted by air and require a medium similar in acoustic properties to tissue, commonly a thick fluid, gel or solid membrane, which displaces air and fills contours between the "eye" or transducer of an ultrasound instrument (such as a probe or scanhead), which converts energy between electrical and acoustic, and the body or object into which the sound is being directed. This medium, by nature of its physical and acoustic properties, serves as an ultrasound acoustic transmission "coupler" between the object of interest and the electronic transducer, thereby acoustically joining the two, so that the sound based information developed can freely pass back and forth between the body and the electronics. Because of the "coupling" effect, this media is commonly referred to as an ultrasound couplant, ultrasound transmission media or acoustic transmission media.

Hydrophilic membranes as coupling media is disclosed, for example, in U.S. Pat. No. 6,039,694 to Larson, et al., which teaches the use of hydrogel films composed of block co-polymers of polyurethane and polyacrylonitrile. The patent discloses application of these materials for ultrasound scanning in the form of shape-conforming films produced by dipping methods, flat membranes that can be stretched over the active surface of an ultrasound probe, scanning through a membrane that is placed in direct contact with skin, and imaging through a latex or other polymeric protective probe cover with such a membrane covering the active area of the transducer and portions of the transducer body. These self-coupling hydrogel films eliminate the requirement for gels and other liquid couplants, and can provide a microbial barrier between the patient and ultrasound probe.

However, by virtue of the composition and mechanical properties, use of films such as those of U.S. Pat. No. 6,039,694 is limited. The films are slippery and lack adhesive characteristics. Such characteristics, while desirable as a scanning surface, tend to allow the membrane to slip off non-horizontal surfaces and slide with the ultrasound probe as it is moved over the surface of the membrane. While the films of U.S. Pat. No. 6,039,694 have sufficient mechanical strength to permit conformal fit by stretching the film over the active face of an ultrasound probe, the absence of adhesive characteristics requires that the membrane be secured to the probe by some mechanical means such as a rubber band or strap.

U.S. Pat. No. 5,522,878 to Montecalvo et al. describes a solid, multipurpose, flexible, ultrasonic, biomedical couplant hydrogel in sheet form to facilitate transfer of ultrasound energy to and from a patient. Also described is a method of attaching the sheet to skin to hold the couplant gel in place during an exam, which constitutes a band of pressure sensitive adhesive bonded to plastic foam, such as foamed rubber, that is located along the outer perimeter of the sheet. The hydrogel sheet so described is not adhesive in and of itself, but depends on an unreliable potential that sufficient perspiration will be present to make the gel somewhat tacky in instances where the chemical composition is such that addition of moisture to the hydrogel will result in some degree of tack. The adhesive border, so described, is not acoustic self-coupling, therefore restricting ultrasound scanning to areas exclusive of those covered with adhesive covered foam.

U.S. Pat. No. 5,782,767 to Pretlow, III, describes a pad assembly for coupling ultrasound from a transducer probe into the human body, wherein a humectant, such as glycerin in combination with water, creates sufficient surface tension for a pad containing a mixture of water and a humectant, such as glycerin, to remain attached to the probe face by the weak forces of surface tension when the pad is extracted from the storage container and placed on skin. Since general scanning procedures normally require large volumes of couplant materials, and the transducer is moved over large areas, such as is done in fetal scanning, the device of U.S. Pat. No. 5,782,767 is limited to single site applications, such as is disclosed by Pretlow for monitoring bladder fullness, rather than as a device for general ultrasound scanning procedures, where its design for such use would not be practical. Use of this device for general scanning would rapidly deplete the glycerin and water mixture, and since the acoustic coupling and the weak forces of surface tension rely upon the presence of this mixture of liquids rather than an engineered adhesive, such general use would to a high degree lead to probable loss of acoustic coupling and separation of the couplant pad from the transducer face.

U.S. Pat. No. 5,394,877 to Orr et al. describes a contact medium structure attachable to externally applied medical diagnostic devices for providing self-adherence of a medical device to the skin of a patient thereby eliminating the need for retaining belts or similar means. A contact medium is described that is inherently adhesive, hydrophilic, skin compatible, ultrasonic compatible and pressure sensitive to facilitate self-adhesion of the medical device to the patient's skin. The device of Orr et al. discloses use as an ultrasound conductive medium, however such device provides only for the attachment of one side the adhesive membrane to the skin of a patient and the opposite adhesive side to a medical device such as a transducer for monitoring purposes, and as such, is limited to use on one site once properly placed. The design of the device of Orr et al. restricts use of medical devices to one area of the body and prevents free gliding motions of a medical device, such as an ultrasound transducer, over the body of a patient, as is necessary for medical imaging procedures. For example, ultrasound imaging over large external areas or imaging from within the body of a patient is inconsistent with its stated use or structural design.

The formulation, manufacture and use of adhesive hydrogels for products that form an interface with skin and tissue Is known to the artisan as is the formulation, preparation and use of adhesive hydrophilic compounds for wound treatment and electrically conductive devices. Adhesive hydrogels are commercially available from producers including 3M Corporation, Ludlow Technical Products and Lectec Corporation. For example, Ludlow Technical Products produces UV cured electrically conductive gels designated Series RG 63B, and E-Beam cured PEO and PVP under the descriptions of GKG-1 and GPPG-1 for wound care.

Adhesive materials can be generally described as being hydophobic or hydrophilic. Examples of hydrophobic adhesives include such familiar items as adhesive tape and bandages. Hydrophobic adhesive materials are most often produced from vinyl based monomers then coated on various flexible polymeric backings which provide for utility as devices to hold other materials such as gauze for maintaining wound dressings in place and in common household uses.

Pressure sensitive hydrophilic adhesives have been developed that provide for a broad range of applications where such materials come into contact with human skin and tissues. Such adhesive materials can be produced by various methods and formulations that provide physical and mechanical properties specific to intended applications. Examples include formulations that produce films and membranes by cross-linking hydrophilic polymers in combination with various humectants, tackifiers, photoinitiators and cross-linkers that under proper conditions providing for efficiencies for wound care, electro-conductive membranes used for physiological monitoring, drug transfer, fluid absorption, in vivo implantation, sealing and adhesion prevention after surgery.

Adhesive hydrogels can be produced by several methods common to the practice that include cross-linking adhesive producing hydrogels by chemical methods, photo-polymerization using ultraviolet light or by high energy means employing gamma or e-beam radiation. The following examples are general descriptions of a range of methods and chemical compounds common to production of such adhesive hydrogels that can be made to demonstrate the mechanical and ultrasound properties necessary for the device of this invention.

Production of adhesive hydrogels for electrical conductivity and wound dressings has been long known in the art. Earlier devices were based on chemical cross-linking using various natural gums and long chain polysaccharides, humectants and takifiers. A formulation containing approximately 55% of a polysaccharide such as karaya when blended with 5 to 10% water, the remainder being hydric alcohols, glycerol being a majority and optionally, the minority propylene glycol, will form adhesive hydrogels when heated in the range of 75 degrees centigrade followed by cooling. Optionally, mechanical properties can be varied by addition of cellulose or other fibrous materials and electrical conductivity enabled by inclusion of alkaline salts in the formulations.

Another example of such formulation and method involves blending a mixture of about 3 to 4% polyvinyl alcohol, 30 to 35% polyvinylpyrrolidone, a hydric alcohol, such as propylene glycol or glycerol in the amount of 20 to 25%, the remainder being water. When the reactants are heated to 125 to 130 degrees centigrade in a suitable reactor, followed by cooling and subsequent casting on a suitable release sheet, an adhesive hydrogel is formed. A scrim composed of woven or non-woven fibers may be added to improve mechanical properties and maintain structural integrity both during casting and in the final product.

The adhesive properties may be varied to better conform to end use by additions of materials such as polyacrylic acid, poly-2-acrylamido 2-methyl propane sulfonic acid, gums and various polysaccharides, i.e., carrageenan, locust bean, karaya and alginate derivatives. Addition of commercially available polymers such as carboxymethyl cellulose, hydroxypropylmethyl cellulose and hydroxyethyl cellulose can also be added to the formulation to alter structural properties.

A further method of producing adhesive hydrogels involves the use thermal or photo-initiating compounds to cross-link solutions of monomers such as acrylic acid, methacrylic acid, or salts thereof, that have been dissolved or dispersed in propylene glycol, glycerol, or other polyhydric alcohols, together with a cross-linking agent which can include, polymercaptans, diethylene glycol diacrylate, trimethylolpropane trithioglycolate, tetraethyleneglycol dimethacrylate, polyethylene glycol, and others, and a thermal or photo polymerization initiator.

Should the desired cross-linking mechanism be that of thermal initiation or used as an adjunct to photo-initiation, useful compounds for such purpose can include benzoyl peroxide, ammonium persulfate, sodium bisulfite and potassium persulfate. In the case where the preferred polymerization mechanism is photo-initiation by ultraviolet radiation, certain dyes or a UV photo initiator such as 2-hydroxy-1[4-(hydroxyethoxy)phenyl]-2-methyl-1-propane can propagate the polymerization mechanism. From a monomer solution consisting of 30% glycerol, 15% acrylic acid, 1% diethylene glycol diacrylate, to which is added 1% 2-hydroxy-1[4-(hydroxyethoxy)phenyl]-2-methyl-1-propane as a photo-initiator, an adhesive hydrogel can be produced by subsequent exposure to UV light for approximately five minutes in the range of 365 nm at an intensity of 10 mw/cm$^2$. By varying the concentration of the cross-linker, the total polymerization time and mechanical properties can be controlled.

In addition to use of chemical and photo-initiated cross-linking to form adhesive hydrogels, high energy radiation sources, primarily E-beam and to a lesser degree gamma, are also used in industrial settings to produce membranes and pressure sensitive adhesive hydrogels for applications such as electrical conductors for physiological monitoring, wound healing and sealants for medical devices.

It is well known that solutions of compounds such as PEO, PVP, and PVA can be cross-linked by gamma and e-beam radiation to form coherent non-adhesive gels. Conversely, U.S. Pat. No. 4,699,146 to Sieverding describes formulations and methods to produce water-insoluble, hydrophilic, pressure-sensitive adhesive membranes that exhibit elastomeric and conformal characteristics. These adhesive hydrogels include irradiation cross-linked synthetic organic polymers, such as PVP and PEO, consisting of three-dimensional matrices, and adhesive plasticizers that due to boiling points are essentially non-volatile. The adhesive hydrogels can be used either as coatings on supporting substrates, such as a woven or non-woven scrim, a release liner or as a self-supporting layer. Sieverding also describes various devices made using such adhesives presenting as bandages, wound dressings, cosmetic masks, electrically conductive and ostomy devices, together with methods for preparing and using the adhesive hydrogels. In one embodiment, the adhesive hydrogel is made electro-conductive by addition of a salt such as magnesium acetate; thereby, making it suitable for attachment to the body for monitoring electrical signals emanating from the body. One such example demonstrates a pressure sensitive, electro-conductive adhesive hydrogel composed of polyvinylpyrrolidone cross-linked by ionizing radiation, a polyalkylene glycol plasticizer, water and a salt selected from ammonium acetate, magnesium acetate or magnesium sulfate.

The cross-linked polymer is produced by irradiation of a solution or dispersion of the gel-forming uncross-linked synthetic organic polymer in a plasticizer that is water-soluble or water-dispersible, and that is capable of dissolving or dispersing the uncross-linked polymer.

Sieverding teaches that the radiation dosage required to produce such adhesive hydrogels is influenced by factors of concentration of the uncross-linked polymer in the plasticizer, and the molecular weight of the uncross-linked polymer. Relatively lower dosages of irradiation are required by a relatively higher concentration of the uncross-linked polymer or a relatively higher molecular weight uncross-linked polymer; whereas, a relatively higher amount of irradiation is required by a relatively lower concentration of the uncross-linked polymer or a relatively lower molecular weight uncross-linked polymer. The composition of the plasticizer and its proportion to the remaining plasticizer, and the uncross-linked polymer also affect the dosage requirements.

In Sieverding's model, irradiation dosages range from about 0.5–7.5 megarads can be used for cross-linking the uncross-linked polymer, with dosages of about 3.5–4.5 megarads being average. For example, a composition containing about 18–22 weight percent, K-90 polyvinylpyrrolidone, about 10–70 weight percent polyethylene glycol having a molecular weight of about 300, and water, dosages in this range are suitable.

Irradiation is used to induce cross-linking of synthetic organic polymers as previously described. The use of high-energy gamma and E-beam irradiation processing techniques enables continuous production of films and coatings facilitates bulk cross-linking and the use of high speed processing techniques, resulting in high volume continuous production of adhesive-coated substances. The uncross-linked solution can be cast directly on a release liner, that may or may not include a woven or non-woven scrim, in a continuous manner, such that the liner continuously moves from the polymer solution casting device through the radiation source, at which point cross-linked adhesive hydrogels are produced.

SUMMARY OF THE INVENTION

The present invention teaches adhesive hydrogels as acoustic coupling media attachable to the active face (transducer) of ultrasound instruments (such as probes or scanheads) and to the inner face of latex, polyurethane or other polymeric probe covers; thereby, enabling the transfer of acoustic energy between an ultrasound probe and an object of interest when used in conjunction with a gel or liquid ultrasound couplant on the skin surface. The adhesive hydrogel comprises acoustic transmission media and is adhesive on both sides of the film. Such adhesive hydrogels films are so comprised as to render desirable levels of acoustic transmission with acceptable low levels of acoustic artifacts, distortion and attenuation.

When such adhesive hydrogel films are adhered to hydrophobic membranes such as the probe covers above described, flexible, self-coupling ultrasound couplants are created such that when used for medical ultrasound imaging, by adherence to the probe face, transmits or "couples" the ultrasound acoustic energy between the transducer and the body.

DETAILED DESCRIPTION OF THE PREFERRED EMBODIMENTS

Applicant has discovered that adhesive hydrogels previously utilized for electrical conductivity, wound care and cosmetic applications, or fixed site adhesion of medical devices, etc., as discussed above, are suitable for application between an ultrasound transducer and a non-adhesive protective sleeve or probe cover as a self-coupling ultrasound transmitting membrane.

The present invention provides a solid, self-coupling membrane that is flexible, conformal to the contour and shape of an ultrasound probe and adhesive on both sides of the hydrogel membrane. The membrane being adhesive on both sides is applied between the transducer and a non-adhesive protective sleeve or probe cover. Thus, with the present invention, the need for a couplant gel inside of the protective sleeve or probe cover is eliminated.

Due to the composition and structure of such membranes, consisting of from 5 to 95% liquid such as water, humectants, compounds for cross linking and preservation, the remainder being polymeric compounds, the membranes are acoustic self-coupling, having acceptable low levels of artifact and distortion. Such membranes possess properties that constitute sufficient tensile and tear strength to withstand mechanical stresses, while in use during imaging exams.

As previously discussed, the adhesive hydrogel can be adhered to the inside a probe cover or sleeve, into which the ultrasound probe is then inserted and attached to the adhesive hydrogel or alternatively, the adhesive hydrogel is first attached to the face of the probe and inserted into the protective cover or sheath, to form an acoustically conductive bond that eliminates the requirement for coupling gels or liquids inside the protective sleeve or probe cover.

Figure 1:
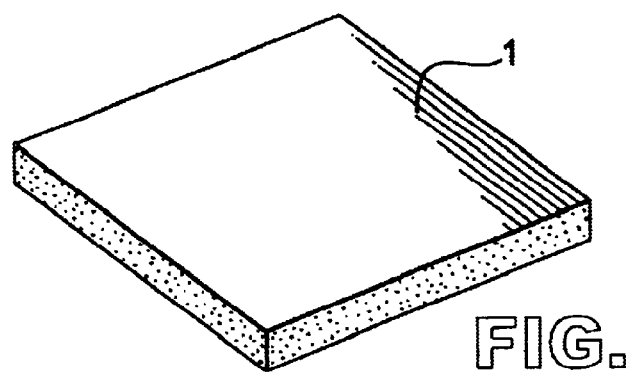
FIG. 1 illustrates an inventive embodiment comprising a single layer adhesive acoustic coupling hydrogel membrane that is adhesive on all surfaces.
Figure 2:
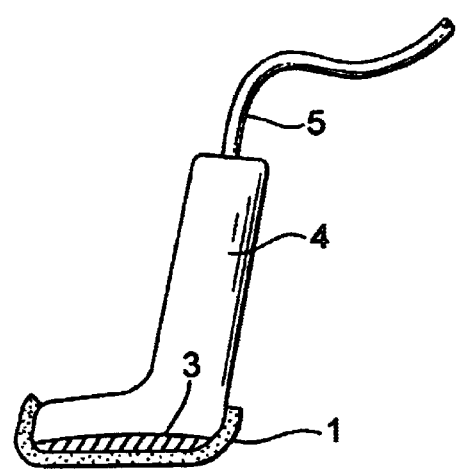
FIG. 2 shows the embodiment of FIG. 1 attached to the active face and body of an ultrasound probe with the other adhesive side prepared for insertion into a protective cover or sheath.
Figure 3:
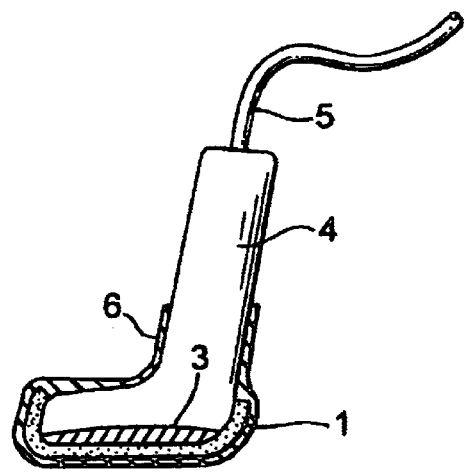
FIG. 3 illustrates the embodiment of FIG. 1 attached to the active face and body of an ultrasound probe and further being covered by a protective sheath.

FIGS. 1 through 3 illustrate, by way of example, the application of adhesive, acoustic self-coupling films of the present invention.

FIG. 1 illustrates a sheet form of the adhesive, conformable, flexible, elastic, uniform, solid acoustic hydrogel sheet according to an embodiment of the present invention. The adhesive membrane 1 is adhesive on both upper and lower sides and may be adhesive throughout the entire thickness. The membrane may contain filaments of hydrophilic woven or non-woven fiber, i.e. a scrim that functions to provide structural stability and top and bottom liners of treated paper or various polymers.

The preferred adhesive hydrogel films are produced with a uniform thickness of about 0.05 to about 1.0 mm. The solid, conformable, ultrasound acoustic coupling hydrogel sheet 1 is homogenous in composition throughout and on all surfaces, and is uniform in thickness, thus providing equal and uniform acoustic energy coupling capacity throughout. The conformal hydrogel sheets 1 can be applied in sizes and thickness as necessary to cover the active surface 3 and optionally the body of the transducer 4 (Fig. 2) and securely attached to the transducer body by virtue of its adhesivity. The solid conformable ultrasound self coupling hydrogel film 1 used in this form of the embodiment, is uniform in composition within and on all surfaces, and in use, is applied to the medical ultrasound transducer active surface 3 by conforming the film over the active surface 3 and adhesively securing the hydrogel film 1 to the body 4 of the transducer.

The homogenous uniform elastic solid ultrasound coupling hydrogel film 1 of this invention provides a desirable level of acoustic coupling with low acceptable levels of artifact and distortion, when applied and integrally conformed to ultrasound transducers of different sizes and shapes.

FIG. 2 Illustrates the adhesive membrane 1 of FIG. 1 attached to the active face 3 and portions of the body 4 of an ultrasound transducer. The adhesive hydrogel 1 encloses, surrounds and tightly conforms to the body 4 of the transducer and is integral to the transducer's active surface 3 so as to form a uniform, solid couplant that is integral and couples a desirable level of acoustic energy between the transducer and a probe cover or protective sleeve and, ultimately, to a target body. The hydrogel conformal film covers all or a portion of the transducer body 4, and is adhesively held in such manner so as to maintain uniform, constant and integral contact of the adhesive hydrogel ultrasound coupling film 1 with the transducer's active face 3 during the ultrasound procedure. The portion of the external surface of the solid, conformal hydrogel film 1 that covers the transducers active surface 3 provides the pathway for acoustic energy transmission or coupling between the transducer and the probe cover or protective sleeve or sheath without the need for a couplant gel inside of the protective sleeve or probe cover.

FIG. 3 illustrates the application whereby an adhesive membrane 1 is adhesively attached to the active face 3 of the transducer thus performing as an ultrasound couplant. The adhesive hydrogel 1 and portions of the transducer body 4 are covered with a probe cover or protective polymeric sleeve or membrane 6 which may act as a microbial barrier for procedures involving imaging in the surgical field, ultrasound guided puncture and intercavity exams.

Furthermore, the embodiment of FIG. 3 enables the transfer of acoustic energy between an ultrasound probe and a target body when used in conjunction with a gel or liquid ultrasound couplant on the skin surface but without the need for a couplant gel inside of the protective sleeve or probe cover.

The adhesive hydrogels may be manufactured by any appropriate process such as those previously discussed in the "Background" portion. The hydrogels of the present invention are not limited to the aforementioned products or compositions but may include such hydrogel compounds, films and membranes that exhibit properties of adhesivity and ultrasound transmission characteristics.

While the invention has been described with reference to preferred embodiments it is to be understood that the invention is not limited to the particulars thereof. The present invention is intended to include modifications which would be apparent to those skilled in the art to which the subject matter pertains without deviating from the spirit and scope of the appended claims.

What is claimed is:

1. An ultrasound acoustic coupling film comprising a hydrogel film having opposed first and second sides with said first and second sides being adhesive, the adhesive hydrogel film being adhered to and positioned between an active area of an ultrasound transducer and a protective sleeve or probe cover whereby with said adhesive film positioned between and in contact with the active area of the ultrasound transducer and the protective sleeve or cover, acoustic coupling is effected and ultrasound energy is transmittable and receivable through the adhesive hydrogel acoustic coupling film thereby eliminating the need for ultrasound couplant gels or fluids within the protective sleeve or cover.

2. The film of claim 1 further comprising filaments of hydrophilic woven or non-woven fiber.

3. A method of conducting ultrasound energy between an ultrasound transducer and a target, said method comprising:
   providing a transducer with an active area for transmitting, or transmitting and receiving, said ultrasound energy,
   positioning an adhesive acoustic coupling hydrogel film having opposed first and second sides with said first and second sides being adhesive between and in adhesive contact with at least the active area of said transducer and a protective sleeve or probe cover, the exterior and interior of which is not adhesive, and;
   transmitting, or transmitting and receiving, said ultrasound energy through the adhesive acoustic coupling film and the probe sleeve or cover, then through a liquid or gel couplant in direct contact with the target being imaged, thus completing the acoustic pathway to facilitate ultrasound imaging.

4. A method of using adhesive hydrogels for conducting ultrasound energy between an ultrasound transducer and a target, said method comprising:
   providing a transducer with an active area for transmitting, or transmitting and receiving, said ultrasound energy,
   positioning an adhesive hydrogel film having opposed first and second sides with said first and second sides being adhesive between and in adhesive contact with at least the active area of said transducer and a protective sleeve or probe cover, the exterior and interior of which is not adhesive, and;
   transmitting, or transmitting and receiving, said ultrasound energy through the adhesive hydrogel film and the probe sleeve or cover, then through a liquid or gel couplant in direct contact with the target being imaged, thus completing the acoustic pathway to facilitate ultrasound imaging.

* * * * *